United States Patent
B et al.

(10) Patent No.: US 12,089,984 B2
(45) Date of Patent: Sep. 17, 2024

(54) HEALTH MONITORING SYSTEM FOR WATER BIRTHS

(71) Applicant: GE Precision Healthcare LLC, Milwaukee, WI (US)

(72) Inventors: Kiran B, Karnataka (IN); Steven M. Falk, Baltimore, MD (US); Rajendra Naik, Karnataka (IN); Arunesh Karthik KS, Karnataka (IN); Vijith Venugopalan, Karnataka (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 323 days.

(21) Appl. No.: 17/725,921

(22) Filed: Apr. 21, 2022

(65) Prior Publication Data

US 2023/0338000 A1    Oct. 26, 2023

(51) Int. Cl.
*A61B 8/00* (2006.01)
*A61B 8/02* (2006.01)
*A61B 8/08* (2006.01)

(52) U.S. Cl.
CPC .............. *A61B 8/02* (2013.01); *A61B 8/0866* (2013.01); *A61B 8/4477* (2013.01); *A61B 8/488* (2013.01); *A61B 2560/0209* (2013.01)

(58) Field of Classification Search
CPC ....................................................... A61B 8/02
See application file for complete search history.

(56) References Cited

U.S. PATENT DOCUMENTS

| | | |
|---|---|---|
| 5,865,733 A | 2/1999 | Malinouskas et al. |
| 10,893,559 B2 | 1/2021 | Prabhakar et al. |
| 2013/0053691 A1 | 2/2013 | Kawabata et al. |
| 2016/0331987 A1 | 11/2016 | Chapman et al. |
| 2022/0104999 A1 | 4/2022 | Maclean |
| 2023/0118324 A1 | 4/2023 | Hong |

FOREIGN PATENT DOCUMENTS

| | | |
|---|---|---|
| EP | 3914148 A1 | 12/2021 |
| WO | 2022206822 A1 | 10/2022 |

OTHER PUBLICATIONS

Non-Final Office Action dated Jun. 26, 2023, U.S. Appl. No. 17/725,807, 35 pages.

*Primary Examiner* — Joseph M Santos Rodriguez

(57) ABSTRACT

A system for monitoring health during a water birth includes a health sensor configured to be coupled to a mother. The health sensor includes a first sensor configured to measure one or more health parameters of a mother, a fetus within the mother or both, a second sensor configured to generate a submerged signal representing whether the health sensor is at least partially submerged in water, and a transmitter configured to transmit communication signals representing data collected by the first sensor. One or more parameters of the communication signals change depending on whether the submerged signal represents that the health sensor is at least partially submerged.

20 Claims, 10 Drawing Sheets

HEALTH MONITORING SYSTEM FOR WATER BIRTHS

BACKGROUND

Water births generally involve a mother undertaking at least a portion of the labor and delivery process while partially submerged in a pool of warm water. The pool may be provided by a tub or tank, which may be general purpose or made specifically for water births. Water birthing is becoming increasingly prevalent, because it may reduce the stress on and discomfort of the mother and the baby.

The health of the mother and fetus are typically monitored during birthing processes, e.g., fetal heartrate, maternal heartrate, and/or uterine activity may be monitored. Electronic monitoring devices typically used to monitor the mother's and/or fetus's vitals are designed to be attached directly to the mother, and to communicate with external equipment. This is well-suited for traditional birthing, because the mother is typically in a bed for at least part of the process, permitting the monitoring devices to communicate with the external equipment wirelessly, through the air, or via cables extending from the monitoring devices coupled to the mother while she is in the bed.

However, in a water birth, the monitoring devices secured directly to the mother are frequently underwater. As such, wireless communication between the monitoring devices and the external equipment is unreliable and/or unavailable. Accordingly, in water births, the monitoring devices attached to the mother communicate with external monitoring devices via cables. However, these devices, secured to the mother and tethered by wires to outside devices, tend to constrain the mother's movements. This can reduce the comfort and mitigate the stress-reduction benefits for the mother during the labor and delivery process.

SUMMARY

Aspects of the disclosure include a system for monitoring health during a water birth. The system includes a health sensor configured to be coupled to a mother. The health sensor includes a first sensor configured to measure one or more health parameters of a mother, a fetus within the mother or both, a second sensor configured to generate a submerged signal representing whether the health sensor is at least partially submerged in water, and a transmitter configured to transmit communication signals representing data collected by the first sensor. One or more parameters of the communication signals change depending on whether the submerged signal represents that the health sensor is at least partially submerged.

In an example, the communication signals include a first signal having a first frequency and a second signal having a second frequency, the first frequency being higher than the second frequency, wherein the transmitter transmits the first signal when the submerged signal represents that the health sensor is not submerged, and wherein the transmitter transmits the second signal when the submerged signal represents that the health sensor is at least partially submerged.

In an example, the first signal has a higher power than the second signal.

In an example, the health sensor includes a first antenna configured to emit the first signal and a second antenna configured to emit the second signal.

In an example, the health sensor is configured to adapt the one or more parameters of the communication signals based on Effective Isotropic Radiated Power.

In an example, the system also includes a converter having a first receiver configured to receive signals from the health sensor that do not travel through water, and a second receiver configured to receive signals from the health sensor that travel through the water.

In an example, the system also includes a monitor in communication with the converter via a wireless or wired connection.

In an example, the first receiver of the converter includes an antenna that extends above a surface of the water, and wherein the second receiver of the converter includes an antenna that extends below the surface of the water.

In an example, the first sensor includes an ultrasonic transducer configured to measure maternal heartrate, fetal heartrate, uterine activity, fetal movement, or a combination thereof.

In an example, the health sensor includes a power management module configured to adjust one or more parameters of the ultrasonic transducer based at least in part on a location of a detected fetal heartrate, so as to preserve battery life of the health sensor.

In an example, the second sensor is configured to measure an impedance of an antenna of the transmitter, or the second sensor is configured to measure a resistivity of an environment in which the health sensor is positioned, or both.

Aspects of the present disclosure also include a method for monitoring health during a water birth. The method includes connecting a health sensor to a mother, measuring one or more health metrics of the mother, a fetus within the mother, or both while the mother is positioned in a tank having water therein, using the health sensor, and transmitting a first signal from the health sensor to a health monitoring device when the health sensor is not submerged in the water. The first signal does not travel through the water. The method also includes transmitting a second signal from the health sensor to the health monitoring device when the health sensor is at least partially submerged in the water. The second signal travels at least partially through the water to the health monitoring device.

In an example, the method also includes determining that the health sensor is at least partially submerged in the water using a first sensor of the health sensor, and selecting to transmit the second signal and not to transmit the first signal in response to determining that the health sensor is at least partially submerged.

In an example, the second signal travels at least partially through the water and at least partially through air to the health monitoring device.

In an example, the first signal has a higher frequency than the second signal.

In an example, the method further includes receiving the first and second signals using a converter connected to the tank, and transmitting a communication signal representing data received in the first signal, the second signal, or both from the converter to the health monitoring device.

In an example, receiving the first and second signals using the converter includes receiving the first signal using a first antenna that extends above a surface of the water, and receiving the second signal using a second antenna that extends below the surface of the water.

In an example, the method also includes adjusting a monitoring signal transmission parameter of the health sensor based on one or more measurements related to fetal heartrate taken by the health sensor.

Aspects of the present disclosure also include a system for monitoring health during a water birth. The system includes a health sensor configured to be coupled to a mother, the health sensor including a first antenna for transmitting first signals through air and not through water, and a second antenna for transmitting second signals at least partially through water. The first signals have a higher frequency than the second signals. The health sensor also includes an ultrasonic transducer configured to measure one or more health parameters of the mother, a fetus within the mother, or both, and a water sensor configured to detect when the health sensor is at least partially submerged in the water. The health sensor further includes a switch module connected to the first and second antenna. The switch module is configured to active the first antenna in response to the sensor detecting that the health sensor is not submerged, and the switch module is configured to activate the second antenna in response to the sensor detecting that the health sensor is submerged in the water. The system also includes a converter, hub, or both configured to receive the first and second signals. The first signals travel through the air to the converter, hub, or both, and the second signals travel at least partially through the water to the converter, hub, or both.

In an example, the converter, hub, or both include a first antenna that extends out of the water and a second antenna that extends in the water.

BRIEF DESCRIPTION OF THE DRAWINGS

The present disclosure may best be understood by referring to the following description and accompanying drawings that are used to illustrate examples of the invention. In the drawings.

DETAILED DESCRIPTION

Figure 1:
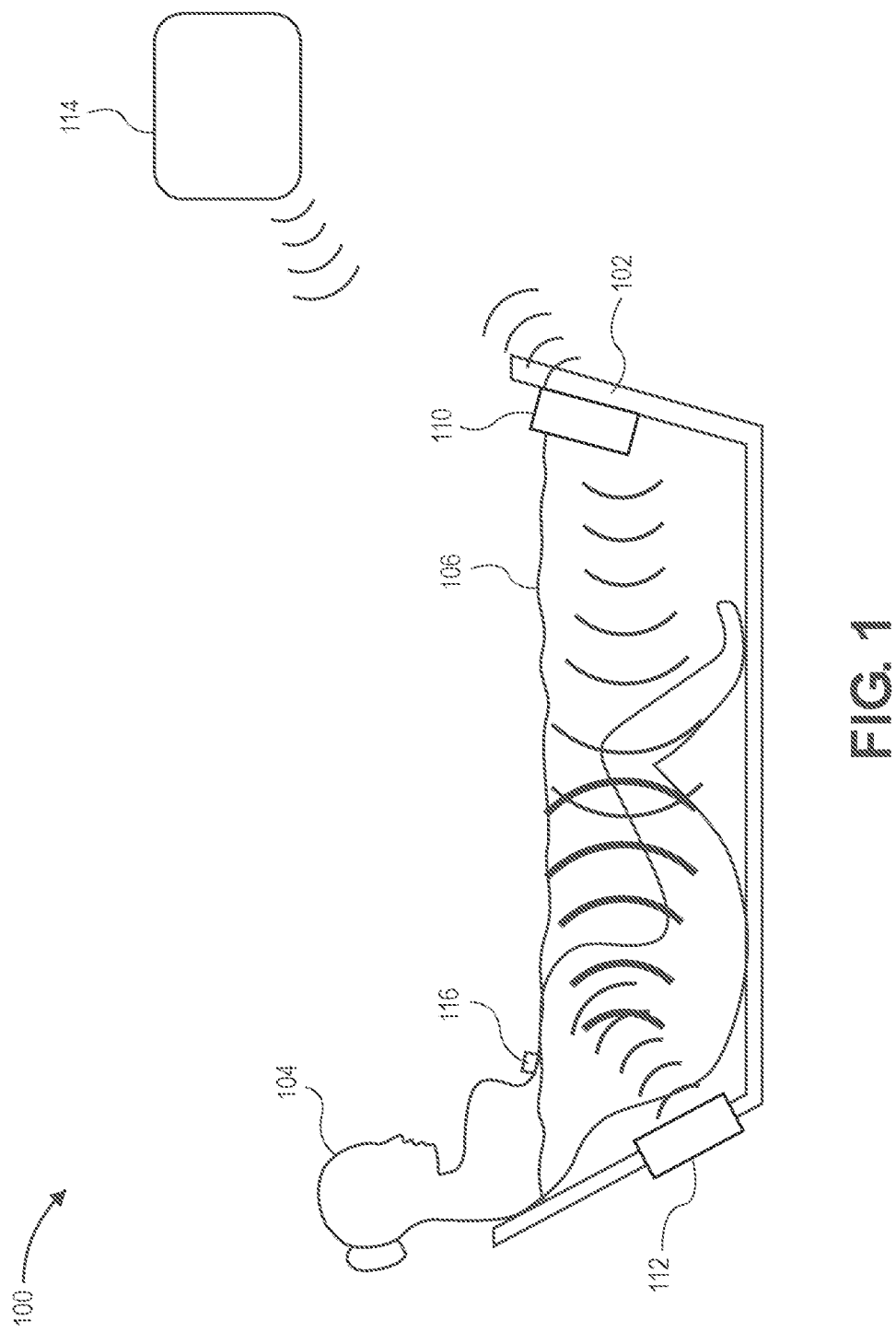
FIG. 1 illustrates a side, schematic view of a health monitoring system for water births, according to an example.

The following disclosure describes several examples for implementing different features, structures, or functions of the invention. Examples of components, arrangements, and configurations are described below to simplify the present disclosure; however, these examples are provided merely as examples and are not intended to limit the scope of the invention. Additionally, the present disclosure may repeat reference characters (e.g., numerals) and/or letters in the various examples and across the Figures provided herein. This repetition is for the purpose of simplicity and clarity and does not in itself dictate a relationship between the various examples and/or configurations discussed in the Figures. Moreover, the formation of a first feature over or on a second feature in the description that follows may include examples in which the first and second features are formed in direct contact, and may also include examples in which additional features may be formed interposing the first and second features, such that the first and second features may not be in direct contact. Finally, the examples presented below may be combined in any combination of ways, e.g., any element from one exemplary example may be used in any other exemplary example, without departing from the scope of the disclosure.

Additionally, certain terms are used throughout the following description and claims to refer to particular components. As one skilled in the art will appreciate, various entities may refer to the same component by different names, and as such, the naming convention for the elements described herein is not intended to limit the scope of the invention, unless otherwise specifically defined herein. Further, the naming convention used herein is not intended to distinguish between components that differ in name but not function. Additionally, in the following discussion and in the claims, the terms "including" and "comprising" are used in an open-ended fashion, and thus should be interpreted to mean "including, but not limited to." All numerical values in this disclosure may be exact or approximate values unless otherwise specifically stated. Accordingly, various examples of the disclosure may deviate from the numbers, values, and ranges disclosed herein without departing from the intended scope. In addition, unless otherwise provided herein, "or" statements are intended to be non-exclusive; for example, the statement "A or B" should be considered to mean "A, B, or both A and B."

| Element | Reference Number |
|---|---|
| Health monitoring system | 100 |
| Tank | 102 |
| Mother | 104 |
| Water | 106 |
| Health sensor | 110 |
| Health sensor | 112 |
| Monitoring device | 114 |
| Beacon | 116 |
| Doppler transducer | 200A, 200B |
| Wireless transceiver | 202A, 202B |
| Health sensor | 300 |
| Housing | 302 |
| Radio transmitter | 304 |
| Antenna | 306 |
| Clip | 307 |
| FHR algorithm module | 308 |
| Doppler receiver module | 310 |
| Doppler transmitter section and steering control module | 312 |
| Array of piezoelectric crystals | 314 |
| Health monitoring system | 500 |
| Health sensor | 502 |
| Converter | 504 |
| Tank | 506 |
| Health monitoring device | 507 |
| Water | 508 |
| First antenna | 510 |
| Second antenna | 512 |
| Hub | 600 |
| Water sensor | 700 |
| Power manager | 702 |
| Radio and switch module | 704 |
| First antenna | 706 |
| Second antenna | 708 |
| Housing | 710 |

-continued

| Element | Reference Number |
|---|---|
| First radio | 800 |
| Second radio | 802 |
| Health sensor | 900 |
| Tank | 902 |
| Water | 904 |
| Health monitoring device | 906 |
| Hub | 908 |
| Monitor | 910 |
| Computing system | 1100 |
| Computer systems | 1101A-D |
| Analysis module | 1102 |
| Processor(s) | 1104 |
| Storage media | 1106 |
| Network interface | 1107 |
| Health monitoring module | 1108 |
| Network | 1109 |

Examples of the present invention may provide one or more of a variety of different technical advantages. For example, the invention may permit monitoring of a mother and/or fetus during water birthing without tethering the mother to communication cables. The invention may also permit free movement of the mother in the birthing tank by steering signals withing the water over a range of directions. The invention may be configured to preserve and extend battery life in the devices employed by dynamically controlling signal types and/or strength of the various monitoring and communication devices. Further, the invention may provide low-loss signals in the context of communication of signals through different media (e.g., water and air).

FIG. 1 illustrates a side, schematic view of a health monitoring system 100, according to an example. The health monitoring system 100 may include or be employed in conjunction with a birthing tank or tub 102. The tank 102 may be a general-purpose bathing tub, or may be constructed specifically for water births. The tank 102 may be an open-air tank, permitting a user (e.g., a mother) 104 to enter and exit the tank 102 by stepping over the side. A pool of water 106 may be held in the tank 102.

The system 100 may also include one or more health sensors (two are shown: 110, 112). It will be appreciated that any number of health sensors may be employed, with the depiction of two in the illustration being merely an example. The system 100 may further include a monitoring device 114, which may be configured for communication with at least one of the health sensors 110, 112. The monitoring device 114 may be configured to interpret the signal received from the health sensors 110, 112 and, e.g., determine health measurements such as heartrate.

In at least some examples, at least one of the health sensors 112 may communicate with the monitoring device 114 via the other health sensor 110, while still being considered to be "in communication with" the monitoring device 114. For example, the sensors 110, 112 may be connected together by a cable or in wireless communication with one another. In other examples, the health sensors 110, 112 may not communicate directly with one another, but may individually communicate directly with the monitoring device 114.

The health sensors 110, 112 may each include one or more transducers, which may be configured to convert electrical power to ultrasonic Doppler signals, or any other suitable signal type. The transducers may also be configured to convert received ultrasonic Doppler signals to electrical signals. For example, as will be described in greater detail below, the health sensors 110, 112 may each include one or more piezoelectric crystals, e.g., a steerable array of piezoelectric crystals, which may be steerable to control a trajectory of the signals, such that echoes therefrom represent one or more health measurements of the mother 104 and/or the fetus, e.g., maternal heartrate, fetal heartrate, uterine activity, and fetal movement. In some examples, each of the health sensors 110, 112 may be capable of transmitting and receiving such ultrasonic Doppler signals. In other examples, one or more of the health sensors 110, 112 may be configured to transmit and not to receive, while another may be configured to receive and not transmit. Various combinations of health sensors may be employed.

The health sensors 110, 112 may be configured to be at least partially submerged in the water, e.g., the internal components are protected from immersion in water. In one specific example, the health sensors 110, 112 may be IP68 rated. Further, the health sensors 110, 112 may be battery operated. Accordingly, the health sensors 110, 112 may transmit and/or receive the Doppler signals directly in the water, e.g., such that the signals do not propagate through any other media (e.g., air, the side of the tank 102, etc.). Without limitation, ultrasound Doppler signals may travel in water with a velocity of from about 1400 m/s to about 1600 m/s, e.g., about 1540 m/s, and thus transmitting and receiving such signals directly in the water using the health sensors 110, 112 may avoid at least some attenuation of the signals.

Further, despite being at least partially submerged, at least one of the health sensors 110, 112 may extend at least partially out of the water 106, such that the health sensors 110, 112 are able to communicate wirelessly with the monitoring device 114. For example, the health sensor 110 may be positioned with an antenna or another transmission device extending upward, beyond the top of the water 106. The health sensor 110 and the monitoring device 114 may be configured to communicate over any type of wireless signal or protocol, such as WIFI®, BLUETOOTH®, medical body area network (MBAN), cellular, etc. In other examples, one or both of the health sensors 110, 112 may be completely submerged and in communication with the monitoring device 114 via one or more cables. In such wired communication examples, the signals that communicate with the mother 104 may be wireless, such that no wires are attached to the mother 104.

In at least some examples, the monitoring device 114 may be configured to coordinate steering of the health sensors 110, 112, e.g., using triangulation for the position of the mother 104 and/or the fetus based on the orientation of the transducers of the respective health sensors 110, 112. That is, the position and orientation of the health sensors 110, 112 may be known at the time an echo signal generated at the mother 104 is received, and thus the position of the mother 104 relative to the sensors 110, 112 in the tank 102 may be calculated.

In some examples, the system 100 may also include a beacon 116, which may be secured to the mother 104. The beacon 116 may be battery-powered, so as to avoid connecting wires to the mother 104. The beacon 116 may be configured to be secured at a reference location on the mother 104. For example, the reference location may be a specific spot on the torso of the mother 104, e.g., marking a point where the fetal heartbeat is initially located. The reference location may thus be used to locate the fetus relative to the mother, so as to monitor the progression of the fetus during birth. Thus, the reference location, in this regard, is not determined relative to the mother's position in the tank 102, but rather provides a basis from which to determine a location of the fetus with respect to the mother's anatomy, during birth.

Additionally, the beacon 116 may permit inferring a location of the mother 104 in the tank 102 relative to the health sensors 110, 112. In particular, the beacon 116 may emit a signal that may be received by the health sensors 110, 112 when the health sensors 110, 112 have a receiver directed thereto, and not otherwise. Thus, the health sensors 110, 112 can "scan" across a range of orientations to acquire the signal from the beacon 116, and then send/receive the Doppler signals toward the beacon 116, as the beacon 116 represents the location of the mother 104. In other examples, the beacon 116 may communicate with other types of sensors, which can relay data sufficient to infer the position of the mother 104 to the monitoring device 114.

Accordingly, the beacon 116 may serve two location functions. First, the beacon 116 may provide a reference point for establishing movement of the fetus relative to the mother 104, as the birthing process progresses. Second, the beacon 116 may permit locating the mother 104 in the tank 102, permitting the signals to be directed or "steered" toward the mother 104.

Figure 2:
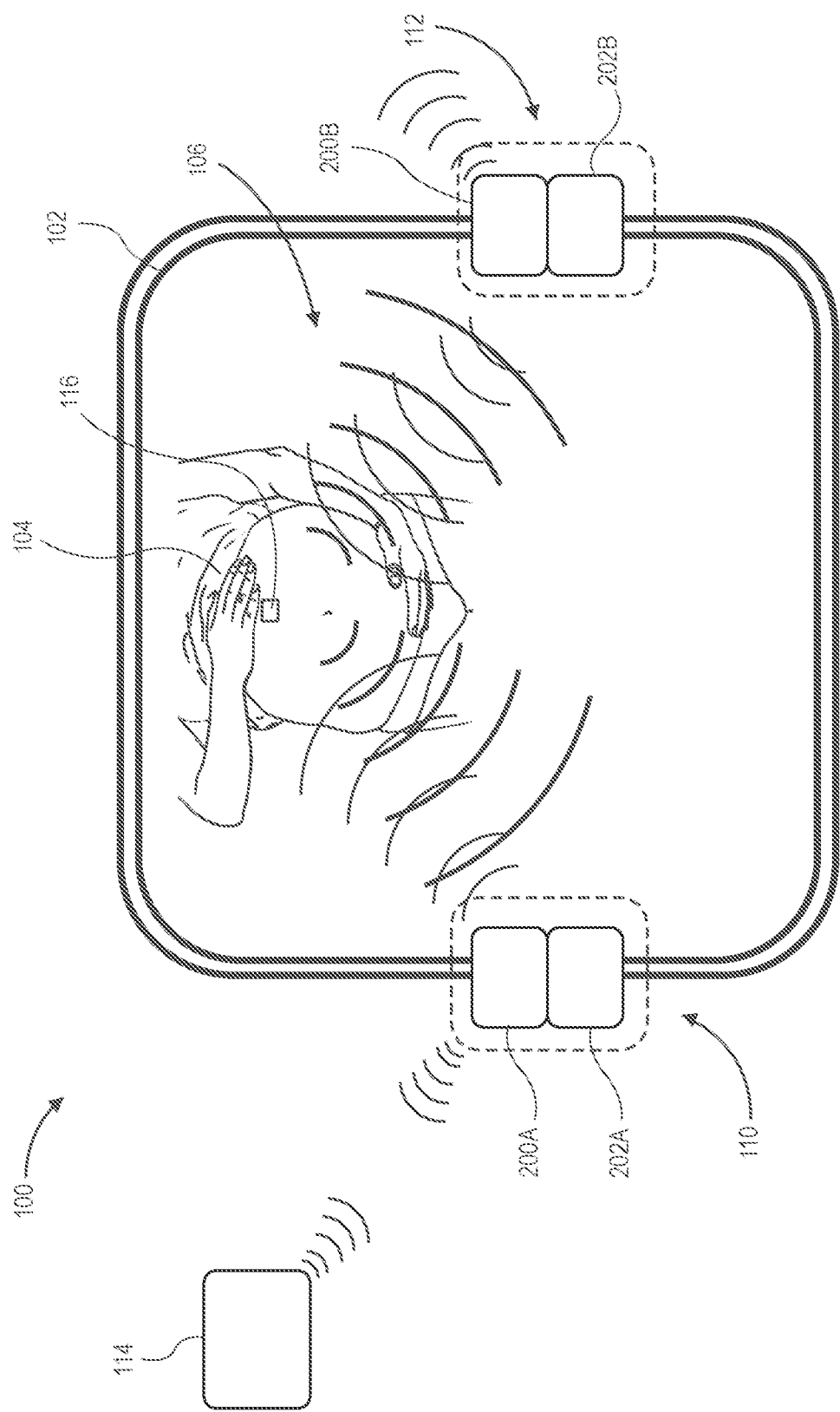
FIG. 2 illustrates a top, plan view of the health monitoring system, according to an example.

FIG. 2 illustrates a top, schematic view of the system 100 and the tank 102, according to an example. It is again noted that the system 100 may include the tank 102, or may be separate therefrom and configured for use therewith. As shown, the health sensors 110, 112 may be connected to the side of the tank 102, e.g., clipped to the rim of the tank 102. In other examples, the health sensors 110, 112 may be secured to the tank 102 in any convenient manner, whether releasable or permanently affixed thereto. For example, the tank 102 may be fabricated with the health sensors 110, 112 embedded therein.

In this example, the health sensors 110, 112 include Doppler transducers 200A, 200B, respectively, and wireless transceivers 202A, 202B, respectively. The wireless transceivers 202A, 202B may be configured for wireless communication (e.g., through the air) with the monitoring device 114. Thus, at least a portion of the wireless transceivers 202A, 202B may be positioned out of the water 106, e.g., held above the water 106 or otherwise outside of the tank 102. As such, any suitable wireless transmission hardware and/or software may be employed for this communication. In other examples, the wireless transceivers 202A, 202B may be replaced with or used in addition to wired communication devices, which may communicate with the monitoring device 114 via one or more cables that are outside of the tank 102.

The Doppler transducers 200A, 200B may be configured to emit and/or receive ultrasonic Doppler signals in the water 106. For example, the Doppler transducers 200A, 200B may cach be configured to convert between electrical power signal and Doppler signal in the water 106. The Doppler transducers 200A, 200B may be independently steered, as mentioned above and described in greater detail below, such that the Doppler transducers 200A, 200B emit Doppler ultrasonic signals that echo from the mother 104 and are received by the transducers 200A, 200B, permitting acquisition of health data from the mother 104, fetus, or both.

Figure 3:
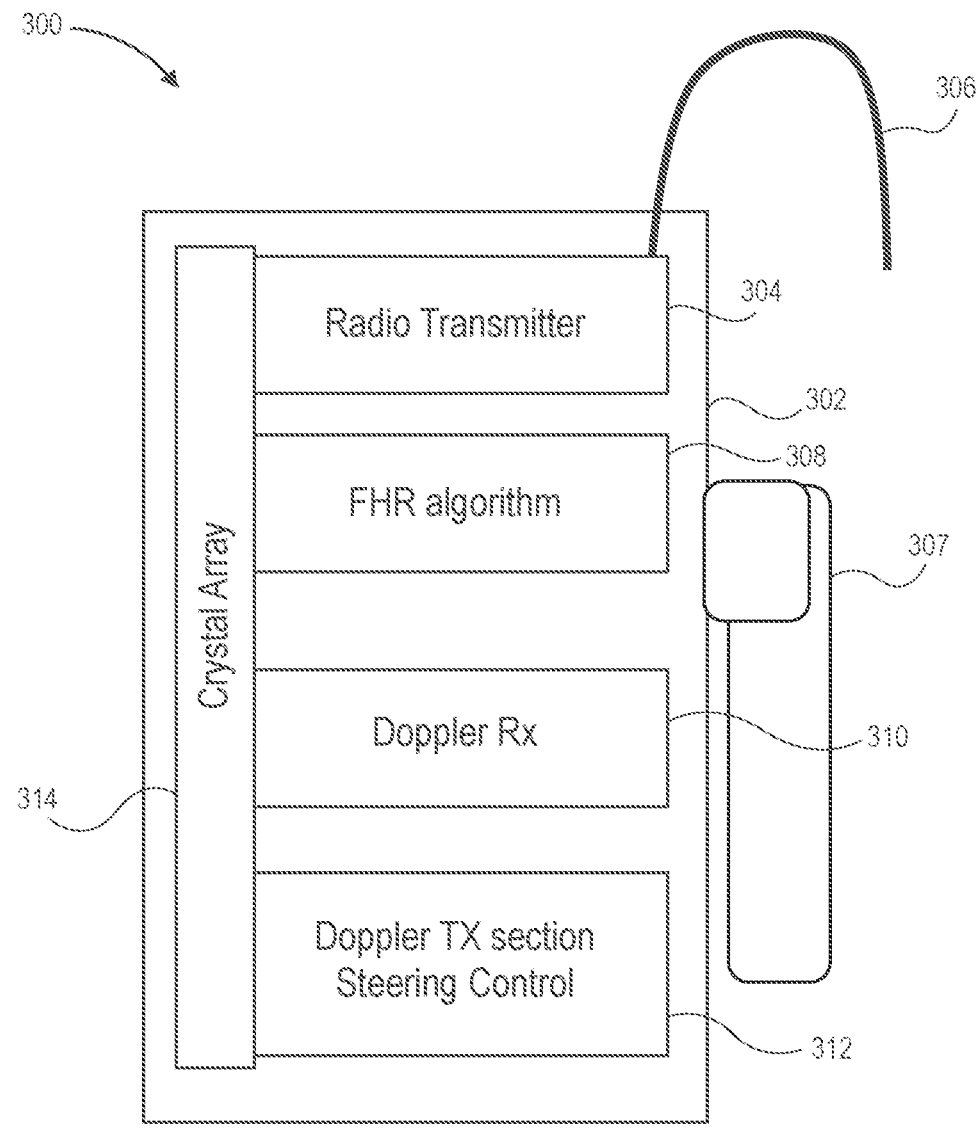
FIG. 3 illustrates a schematic view of a health sensor of the health monitoring system, according to an example.

FIG. 3 illustrates a schematic view of a health sensor 300, according to an example. The health sensor 300 may be implemented by one or both of the health sensors 110, 112 discussed above. The health sensor 300 may include a housing 302, which may be configured to protect components therein from immersion in water. Within the housing 302, there may be a radio transmitter 304, which may be configured to communicate wirelessly with a computing device (e.g., the monitoring device 114 of FIGS. 1 and 2) via an antenna 306. In this example, the antenna 306 is an external antenna, extending at least partially upwards from the housing 302. In other examples, the antenna 306 may be internal to the housing 302. A clip 307 may be secured to the housing 302 and may be configured to connect the housing 302, and thus the health sensor 300, to a rim of a tank (e.g., the tank 102). In other examples, other types of mounting devices may be employed.

The health sensor 300 may also include a fetal heartrate (FHR) algorithm module 308, which may be positioned within the housing 302. The FHR algorithm module 308 may be configured to infer a fetal heartrate from Doppler signals and, e.g., to separate the fetal heartrate signals from maternal heartrate signals. For example, the fetal heartrate may be at a different frequency than the maternal heartrate, and thus may be distinguished based on this or any other signal characteristic.

A Doppler receiver module 310 and a Doppler transmitter section and steering control module 312 may also be included within the housing 302. Further, an array (e.g., one dimensional, two dimensional, radial, etc.) of piezoelectric crystals 314 may also be included within the housing 302, which may serve as the transducers for the sensor 300. For example, the piezoelectric crystals of the array 314 may receive electrical signals from the Doppler transmitter and steering control module 312 and convert these signals to Doppler signals that propagate through the water. The crystals of the array 314 may also receive Doppler signals (echoes) from the water and convert them to electric signals. The array 314 may be positioned within the housing 302 so as to be at least partially below the surface of the water, thereby permitting the array 314 to transmit Doppler signals and receive echoes directly in the water.

Further, the array 314 may be steerable, e.g., by changing the orientation of one or more crystals of the array 314, so as to direct the Doppler signals to and receive signals from a desired location. In at least some examples, the Doppler transmitter section and steering control module 312 may control the directionality of the Doppler signals by adjusting the orientation of the crystals of the array 314, or signaling the array 314 to adjust, e.g., using another actuator. The Doppler transmitter section and steering control module 312 may include software configured to control a scan of different orientations for the array 314, so as to direct the Doppler signals.

Figure 4:
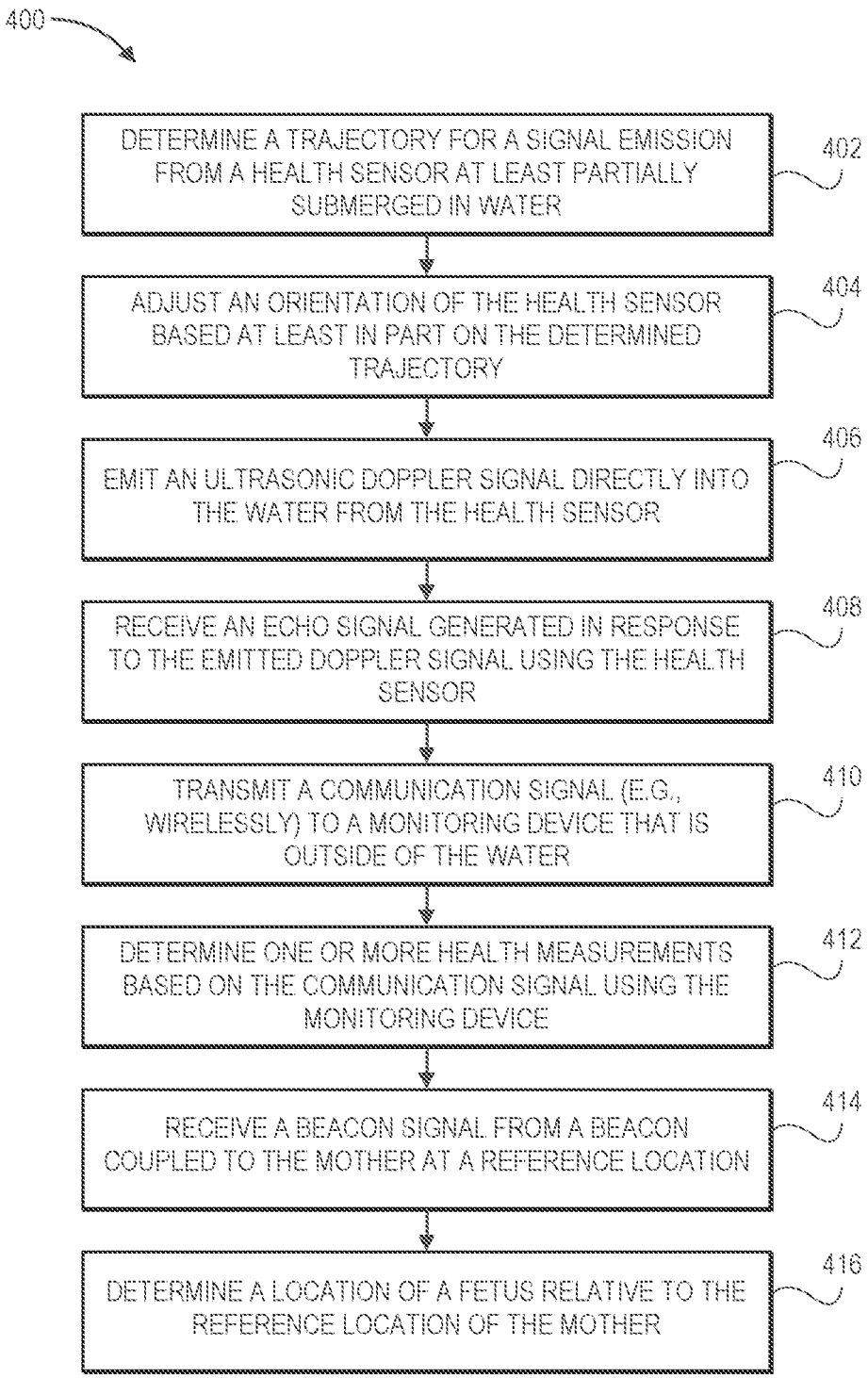
FIG. 4 illustrates a flowchart of a method for monitoring health during a water birth, according to an example.

FIG. 4 illustrates a flowchart of a method 400 for monitoring a health measurement of a mother, a fetus, or both in a water birth, according to an example. The method 400 may employ one or more examples of the system 100 discussed above with reference to FIGS. 1-3, and is thus described herein with reference thereto. In other examples, however, the method 400 may implement any other heath monitoring system. Further, the steps of the method 400 may be executed in the order presented herein, or in any other order, whether in parallel or in sequence. Additionally, one or more of the steps may be partitioned into two or more steps, and/or any two or more of the steps may be combined into a single step.

The method 400 may include determining a trajectory for a signal emission from the health sensor(s) 110, 112, which may be submerged in water, as at 402. In one example, the health sensors 110, 112 may perform a raster scan. In such a raster scan process, the health sensors 110, 112 may transmit in a plurality of different directions, in sequence, and determine which of the directions results in an echo being received. As noted above, this may be controlled by the Doppler transmitter and steering control module 312 of the individual health sensors 110, 112.

The scanning procedure may stop when an echo is received, or may continue through a predetermined range, and then return to a trajectory that generated useable (e.g., the strongest) echoes representing the desired health measurements. In another example, in which the system 100 includes the beacon 116 that emits beacon signals, the health sensor 110 may orient its transducer(s) in a plurality of different directions until receiving the beacon signal. The health sensor 110 may thus determine the direction for the transducers thereof based at least in part on whether a beacon signal is acquired at any scanned direction. In this latter example, the health sensor 110 may not transmit Doppler signals during the scan, but may rather "listen" for signals from the beacon 116. In other examples, the health sensor 110 may transmit Doppler signals while scanning for beacon 116 signals. Further, in still other examples, the direction for the signals to be emitted may be determined based on other sensors receiving signals from the beacon 116.

In at least some examples, the mother 104 exiting the tank 102 may cause the system 100 to be unable to acquire an echo signal that includes health monitoring information. The system 100 may thus be configured such that the health sensors 110, 112 stop looking for an echo after passing through a range of orientations, or may continue to scan until an interrupt is received (e.g., a button pressed, e.g., on the monitor 114, in response to the mother 104 exiting the tank 102). In at least some examples, the failure to acquire an echo signal may trigger an alarm.

The method 400 may also include adjusting an orientation of the transducers of the health sensor, as at 404. This adjustment may be based at least in part on the determination made at 402 and may be implemented internal to the individual health sensors 110, 112. In some examples, the determining at 402 and the adjusting at 404 may occur simultaneously, e.g., as part of the same process of orienting the transducers in an appropriate direction. In other examples, for example, the orientation may be determined in 402 and then refined based on a strength of the echoes by further adjusting at 404. In some examples, the steps 402 and 404 may be repeated continuously, at relatively short intervals, or at any time an echo representing a health measurement is not received.

The method 400 may further include emitting an ultrasonic Doppler signal directly into the water 106 in the trajectory determined at 402, as at 406. As noted above, the health sensor(s) 110, 112 may be at least partially submerged in the water 106, and thus the transducers (e.g., arrays of piezoelectric crystals) may be permitted to communicate directly with the water 106. However, the health sensor(s) 110, 112 may be separated from the mother 104, and may not be connected to the mother 104. As such, the mother 104 may not be tethered to the health sensor(s) 110, 112 via cables.

The method 400 may also include receiving an echo signal generated in response to the emitted signal, using the health sensor(s) 110 and/or 112, as at 408. The echo signal may be received directly from the water 106 by the health sensor(s) 110, 112, which may maintain low attenuation in the echo signal. Further, artifacts (noise) in the signal generated by waves or other water movement, echoes from the signal reflecting off the tank 102, etc., may be muted during processing, e.g., based on models of expected data signals (e.g., known characteristics of maternal heartrate, fetal heartrate, and/or uterine activity signals).

One or more communication signals may then be transmitted (e.g., wirelessly) from the health sensor(s) 110, 112 to the monitoring device 114, as at 410. The one or more communication signals may carry data representing the echo signals. The health sensor(s) 112, 112 may include an external antenna that may extend out of the water to permit communication of the signals wirelessly to the monitoring device 114.

The echo signal received by the health sensor(s) 110, 112 may provide data representing one or more health-related properties of the mother and/or fetus. This data may be transmitted (e.g., wirelessly) to the monitoring device 114 for interpretation. That is, the monitoring device 114 may determine one or more health measurements based on the communication signal, which is generated based on the echo signals, as at 412. For example, the echo signal may represent a maternal heartrate and/or a fetal heartrate. The maternal heartrate and the fetal heartrate may be distinguished, e.g., using the monitoring device 114, based on different characteristics of a maternal heartrate and a fetal heartrate, based on the differences therebetween in frequency, signal strength, or any other signal parameter. In addition, based on location of the source, heartrates for twins, triplets, etc., may be distinguished and, e.g., separately monitored. In at least some examples, the health sensor(s) 110, 112 and/or the monitoring device 114 may filter and/or process the physiological parameter (e.g., health data) represented by the echo signals, permitting or actively inferring fetal heart rate for transmission via the communication signals.

As noted above, in at least some examples, the system 100 may include a beacon 116 for locating the mother 104 in the tank 102 and steering the health sensors 110, 112, as noted above in steps 402 and 404. Additionally, the beacon 116 may be coupled to the mother 104 at a reference location. The reference location may be selected to coincide with a location of a signal of the fetal heartbeat, and the reference location may remain stationary on the mother 104, while the fetus moves with respect thereto. Such changes in position of the fetus relative to the reference location of the mother 104 may thus provide insight into the progression of the birthing process.

In such examples, the method 400 may include receiving the beacon signal from the beacon 116 coupled to the mother 104 at the reference location, as at 414. The beacon signals may be ultrasonic, and thus may be acquired by the health sensor(s) 110, 112. Although ultrasonic, the beacon signals may be of a different frequency than (or otherwise distinguishable from) the Doppler signals and/or echoes therefrom.

Further, based on the orientation of the health sensors 110, 112, the reference location of the beacon 116 may be determined, e.g., using the monitoring device 114 or by communication/coordination between the health sensors 110, 112. Similarly, the location of the fetal heartbeat may also be determined from the echo signals. As at 416, the two locations inferred based on the beacon and echo signals may then be compared so as to determine a location (and/or movement) of the fetus during the birthing process. Similarly, the mother's heartrate signal originates from a fixed location relative to the reference location of the beacon 116. Accordingly, the mother's heartrate may be distinguished based on its location relative to the beacon 116, which may be different from the fetal heartrate source. Thus, the stationary position of the mother's heart relative to the beacon 116 and the different locations of the mother's heart and the fetal heart(s) may be employed to distinguish between the two signals.

Figure 5:
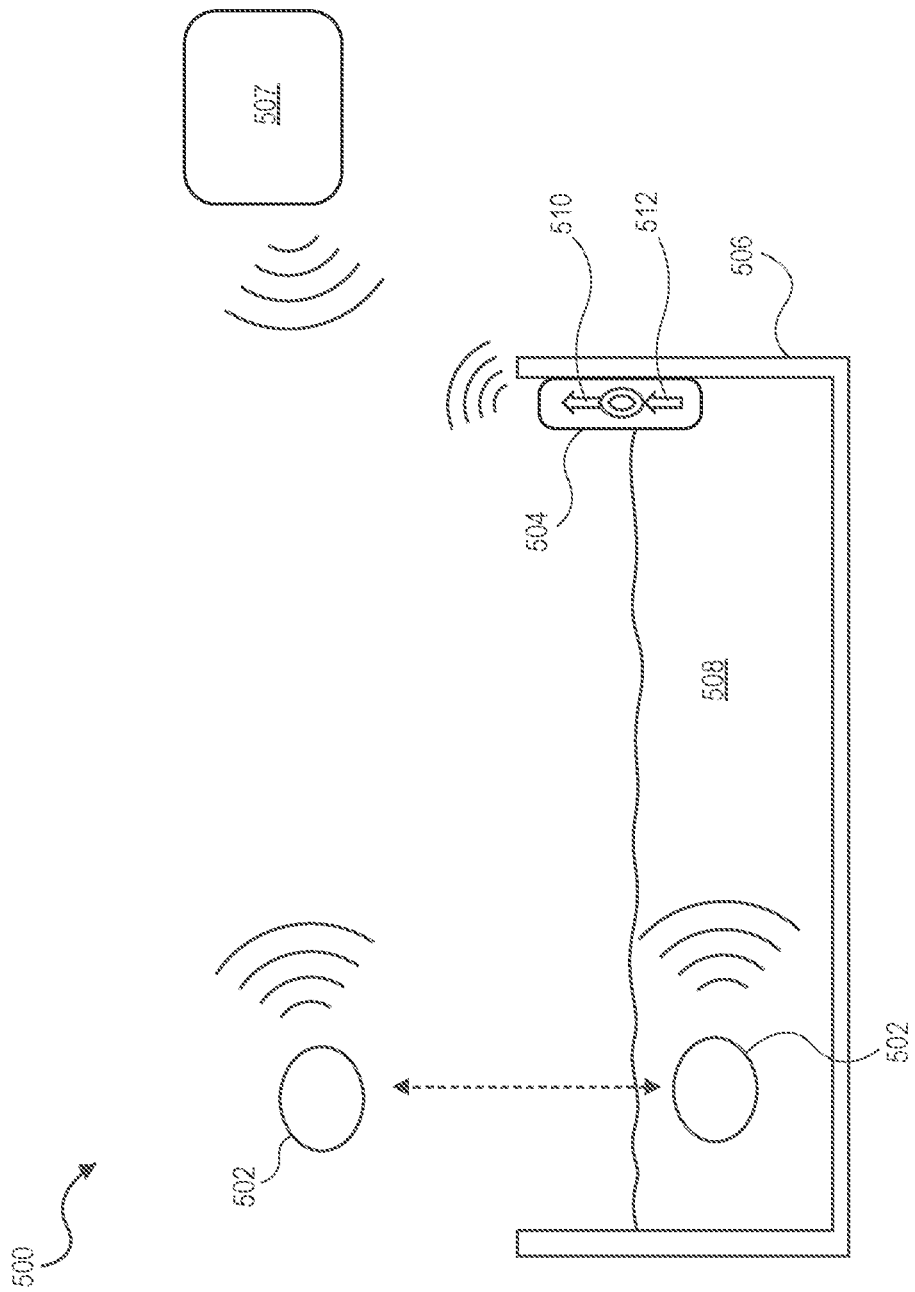
FIG. 5 illustrates a side, schematic view of another health monitoring system, according to an example.

FIG. 5 illustrates a side, schematic view of another health monitoring system 500, according to an example. Like the health monitoring system 100, the health monitoring system 500 may be configured to monitor a health of a mother, fetus within the mother, or both during a water birth. The system 500 may generally include a health sensor 502, a converter 504, and a health monitoring device 507. Further, the system 500 may include or be configured for use with a tank 506 that holds water 508.

The health sensor 502 may be connected directly to the mother via straps, bands, etc., and may be configured to detect maternal heartrate, fetal heartrate, uterine activity, and/or other metrics related to the health of the mother, fetus, or both. For example, the health sensor 502 may include one or more ultrasonic transducers configured to send and receive, e.g., Doppler, signals and, in some examples, to process the monitoring signals into communication signals which may be relayed to the converter 504.

The health sensor 502 may be configured to transmit at least two different "types" of communication signals for reception by the converter 504. The different "types" of sensors discussed herein may be radiofrequency or other electromagnetic signals, but with different characteristics, such as frequency band, power, etc. The different signal types may be generated by different antenna or by a single antenna, as discussed herein. For example, the first signal type may be a BLUETOOTH, WIFI, or MBAN signal, which may be provided for transmission through air to the converter 504. In some examples, the frequency of the first signal type may be 2.4 GHZ, 5 GHZ, or a combination thereof. Other frequency spectra may also be employed for such wireless signal transmission through the air. Thus, the first signal type may be transmitted when the health sensor 502 is above the surface of the water 508.

The second type of signal may be a relatively low frequency (as compared to the first signal type) signal, suitable for transmission through the water 508. For example, the frequency of the second signal may be less than about 1 GHZ, less than about 800 MHZ, or less than about 600 MHz. In some examples, WMTS or ISM band frequencies may also or instead be used.

The health sensor 502 may be configured to automatically determine which signal type to use and, in response, activate circuitry configured to transmit data using the selected signal type. For example, the health sensor 502 may include a water sensor that detects whether the health sensor 502 is submerged in the water 508, and may generate a submerged signal indicative of whether the health sensor 502 is at least partially submerged. A variety of such sensors are known and may be employed. In at least some examples, changes in impedance in the antenna of the health sensor 502 or other current leakage techniques may be employed to detect when the health sensor 502 is submerged.

The health sensor 502 may be battery-operated, so as to avoid attaching wires or cords to the mother during the water birth. In at least some examples, one or more techniques may be employed to conserve the battery of the health sensor 502. For example, the health sensor 502 may be configured to transmit a lower power when submerged and using the second signal type, as the distance over which the signal transmits may be expected to be relatively short, e.g., constrained by the dimensions of the tank 506. Further, the monitoring signals sent from the health sensor 502 into the mother may be adjusted to prolong battery life. For example, the duration of the signal transfer pulses may be dynamically adjusted based on closed-loop monitoring of the signal strength and fetal heartrate. This may account for different depths of the fetal heart, as a function of distance from the health sensor 502 located on the exterior of the mother. For example, a 90 ms signal can be reduced based on a consistent heartbeat detection.

As noted above, the system 500 also includes the converter 504. The converter 504 serves to receive both of the first and second types of signals from the health sensor 502. For example, the converter 504 may be positioned at the surface of the water 508, and may include a first antenna 510 that is configured to receive the first signal type and a second antenna 512 that is configured to receive the second signal type. The first antenna 510 may extend upward, above the water 508, and the second antenna 512 may extend downward into the water 508. In some examples, the converter 504 may be buoyant, with the lower end thereof weighted, so as to maintain the second antenna 512 below the surface of the water 508 and the first antenna 510 above the surface. In other examples, the converter 504 may be coupled to the wall of the tank 506. In such examples, the water level may be controlled with respect to the position of the converter 504, or, alternatively, the first antenna 510 may extend to a position above the tank 506 while the second antenna 512 extends to a position proximal to the bottom of the tank 506, e.g., to ensure that the first antenna 510 is not entirely submerged, while the second antenna 512 is at least partially submerged, without regard to the specific water level.

The converter 504 may be configured to communicate with the health monitoring device 507. As shown, the converter 504 may be configured to communicate with the health monitoring device 507 wirelessly, e.g., through the air via another antenna or via the first antenna 510. In some examples, the converter 504 may also or instead be configured to communicate with the monitor 506 via one or more cables.

The monitor 506 may be configured to receive data from the converter 504. Further, the health monitoring device 507 may include one or more processors configured to process raw sensor data from the converter 504 into health metrics providing useful information about fetal heartrate, maternal heartrate, uterine activity, and/or other metrics. For example, the health monitoring device 507 may provide a user interface, display, input devices, etc. The health monitoring device 507 may also be configured to make determinations about the health of the mother, fetus, or both, and provide outputs, initiate alarms, etc., based thereon.

Figure 6:
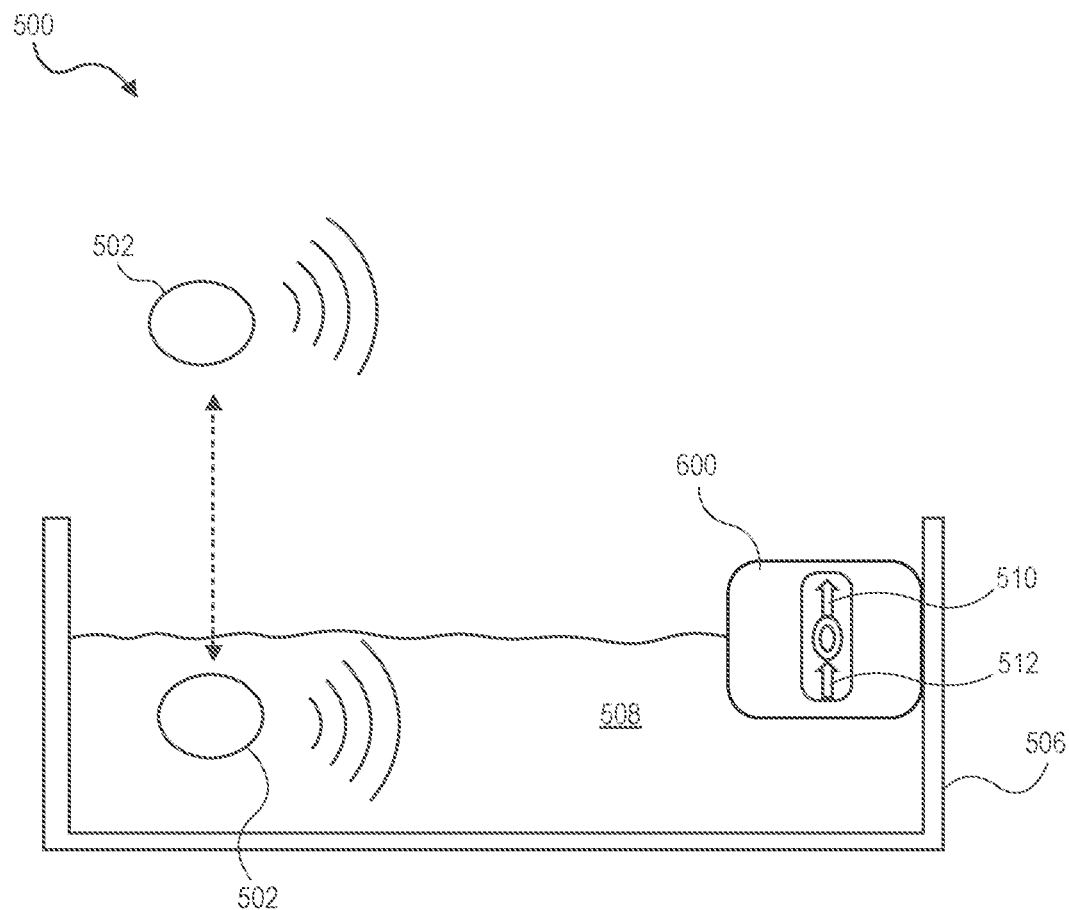
FIG. 6 illustrates a side, schematic view of another example of the system.

FIG. 6 illustrates a side, schematic view of another example of the system 500. In this example, the converter 504 and the monitor 506 are integrated into a hub 600. The hub 600 may be configured to receive both the first and second signal types and may include the first and second antennae 510, 512. Further, the hub 600 may be configured to convert the data transmitted via the communication signals from the health sensor 502 into health data.

Figure 7:
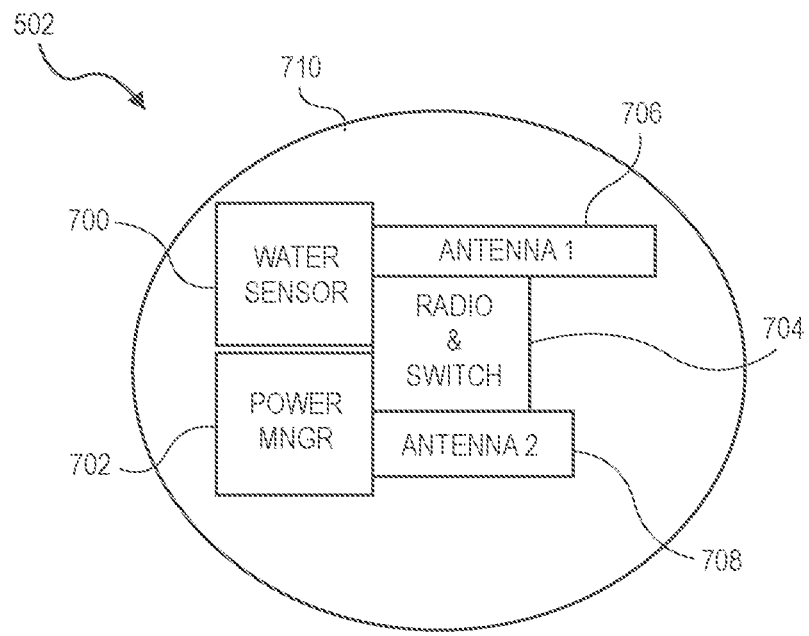
FIG. 7 illustrates a schematic view of the health monitoring device, according to an example

FIG. 7 illustrates a schematic view of the health sensor 502, according to an example. As shown, the health sensor 502 may include a water sensor 700, a power manager 702, a radio and switch module 704, a first antenna 706, and a second antenna 708. These components may be packaged in a housing 710, which may be configured to survive and protect the components while the housing 710 is submerged in the water 508 (e.g., FIG. 5).

The water sensor 700 may be any suitable type of water sensor. Various humidity sensors, water-level sensors, resistivity sensors, impedance sensors, current leakage sensors, etc. are known and may be employed to provide input to the health sensor 502 that permits the health sensor 502 to determine whether it is submerged.

The power manager 702, as noted above, include a battery and may be configured to provide power management functionality to preserve battery life. Accordingly, the power manager 702 may make determinations as to signal transmission strength, e.g., for the communication signals and/or the health monitoring signals that are directed into the mother to detect health metrics. For example, the power manager 702 may dynamically and successively lower signal communication strength in response to the converter 504 (e.g., FIG. 5) receiving signals. That is, the power manager 702 may reduce signal strength until the converter 504 fails to reliably receive the communication signals. This may apply for the first signal type, the second signal type, or both. Additionally, the power manager 702 may reduce the frequency at which the health monitoring signals are pulsed, the duration of the pulses, or both, e.g., based on the depth of the fetal heartrate, consistency of the measurements, and/or other factors.

The first antenna 706 may be configured to transmit the first signal type, and the second antenna 708 may be configured to transmit the second signal type. Accordingly, the radio and switch 706 may select which antenna to activate, based on whether the first signal type or the second signal type is to be transmitted. The first antenna 706 and the second antenna 708 may be configured to send different signal frequencies, at different power levels, or both. Further, the first antenna 706 may be oriented in a generally upward direction and the second antenna 708 oriented in a generally downward direction, such that partial submersion of the health sensor 502 may result in the first antenna 706 extending out of the water, the second antenna 708 extending in the water, or both. In at least some examples, the first antenna 706 and the second antenna 708 may be representative of a single, adjustable antenna that may be dynamically configured to transmit in either the frequency of the first signal type or the frequency of the second signal type.

Figure 8:
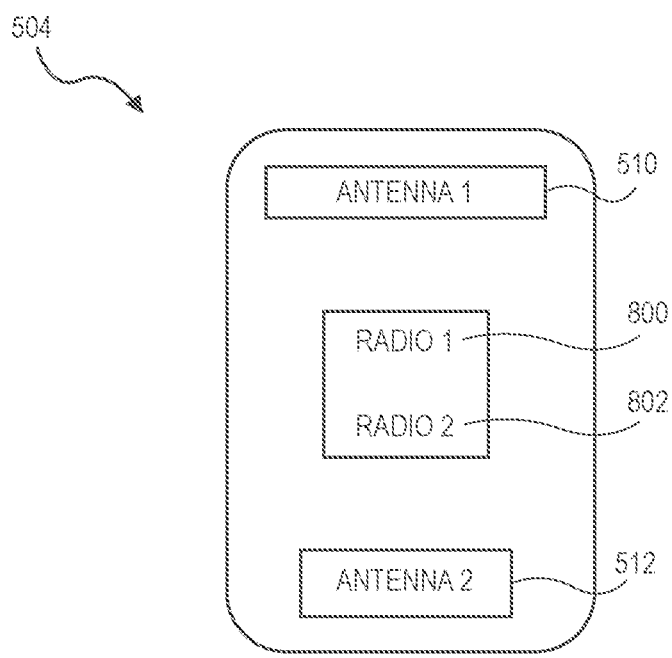
FIG. 8 illustrates a schematic view of the converter, according to an example.

FIG. 8 illustrates a schematic view of the converter 504, according to an example. The converter 504 may be configured to receive at least two different types of signals, aggregate the data received in both signal types, and send such aggregated data to the health monitoring device 507, as noted above. Thus, the converter 504 may include the first antenna 510 and the second antenna 512, as noted above. Further, the converter 504 may include a first radio 800 and a second radio 802. The first radio 800 may be configured to receive and/or send signals via the first antenna 510, and the second radio 802 may be configured to receive and/or send signals via the second antenna 512. Further, the converter 504 may include a housing 806, which may be at least partially water-resistant, such that at least the second antenna 512 may extend below the surface of the water. In at least some examples, the first antenna 510, the second antenna 512, or both may be external to the housing 506. In at least some examples, the housing 506 may include one or more structures or devices configured to permit the housing 506 to be attached to the wall of the tank 506 (e.g., FIG. 5).

Figure 9:
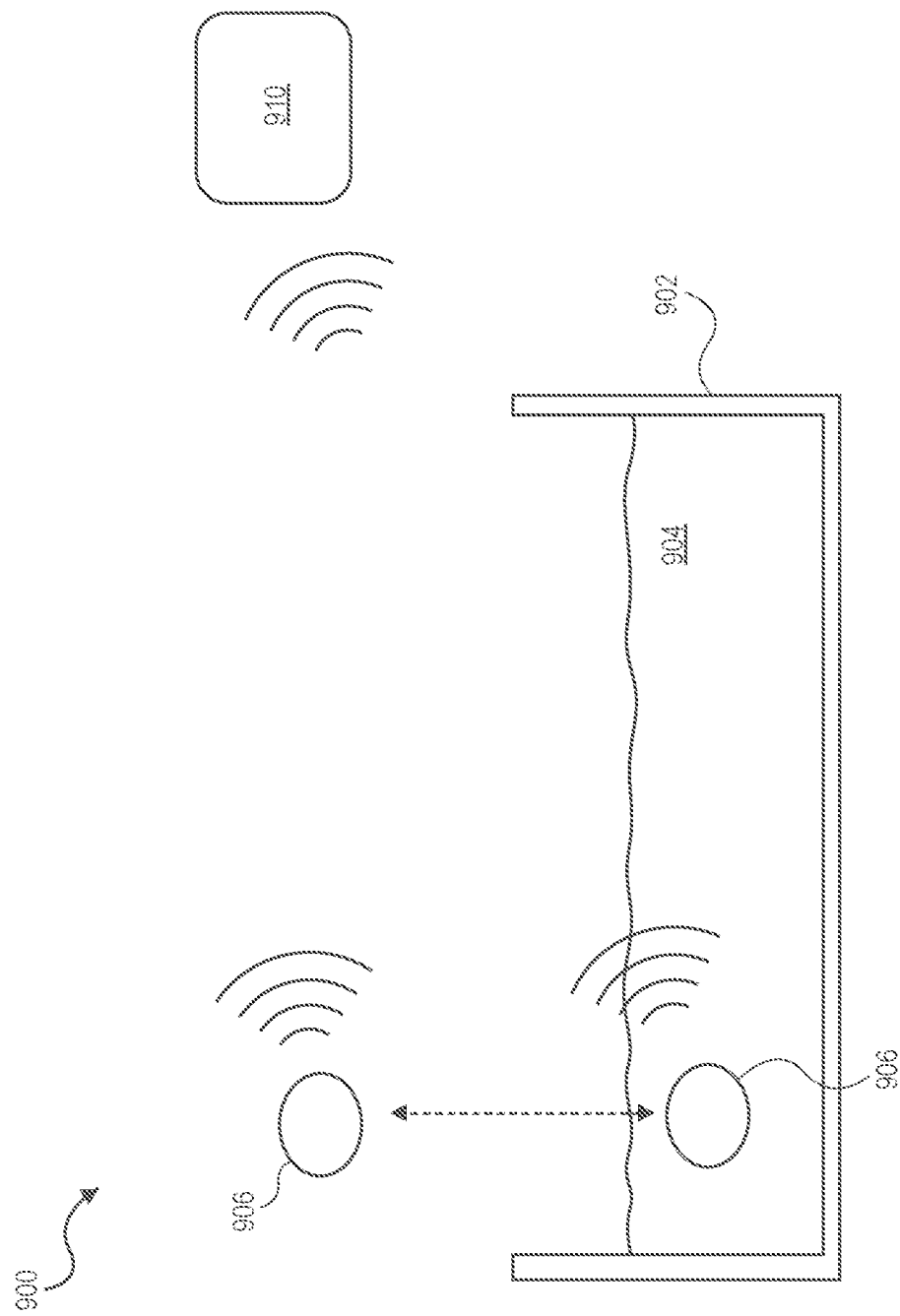
FIG. 9 illustrates a flowchart of a method for monitoring a health of a mother, a fetus, or both during a water birthing, according to an example.

FIG. 9 illustrates a schematic view of another health monitoring system 900, according to an example. The health monitoring system 900 may include a tank 902 at least partially filled with water 904 for a water birth. The health monitoring system 900 may include a health sensor 906, which may be connected to the mother, and may be cordless, so as to permit the mother to move freely into/out of and within the tank 502.

Additionally, the device 906 may be configured to transmit signals, and more particularly, may be configured to modulate the signal properties depending on whether the device 906 is submerged in the water 904 or above/out of the water 904, as shown. For example, the device 900 may be configured to determine when it is submerged, e.g., using an impedance sensor, as discussed above. In response to determining that the device 906 is not submerged, the device 906 may transmit a signal having a high frequency and power, tailored for air-only transmission and reception at a monitor 910. In response to determining that the device 906 is at least partially submerged below the surface of the water 904, the device 906 may be configured to adaptively modulate the signal and/or frequency so as to ensure an Effective Isotropic Radiated Power (EIRP) link budget is maintained. Thus, two different types of signals may be transmitted, either from a single antenna or from two or more antennae.

Figure 10:
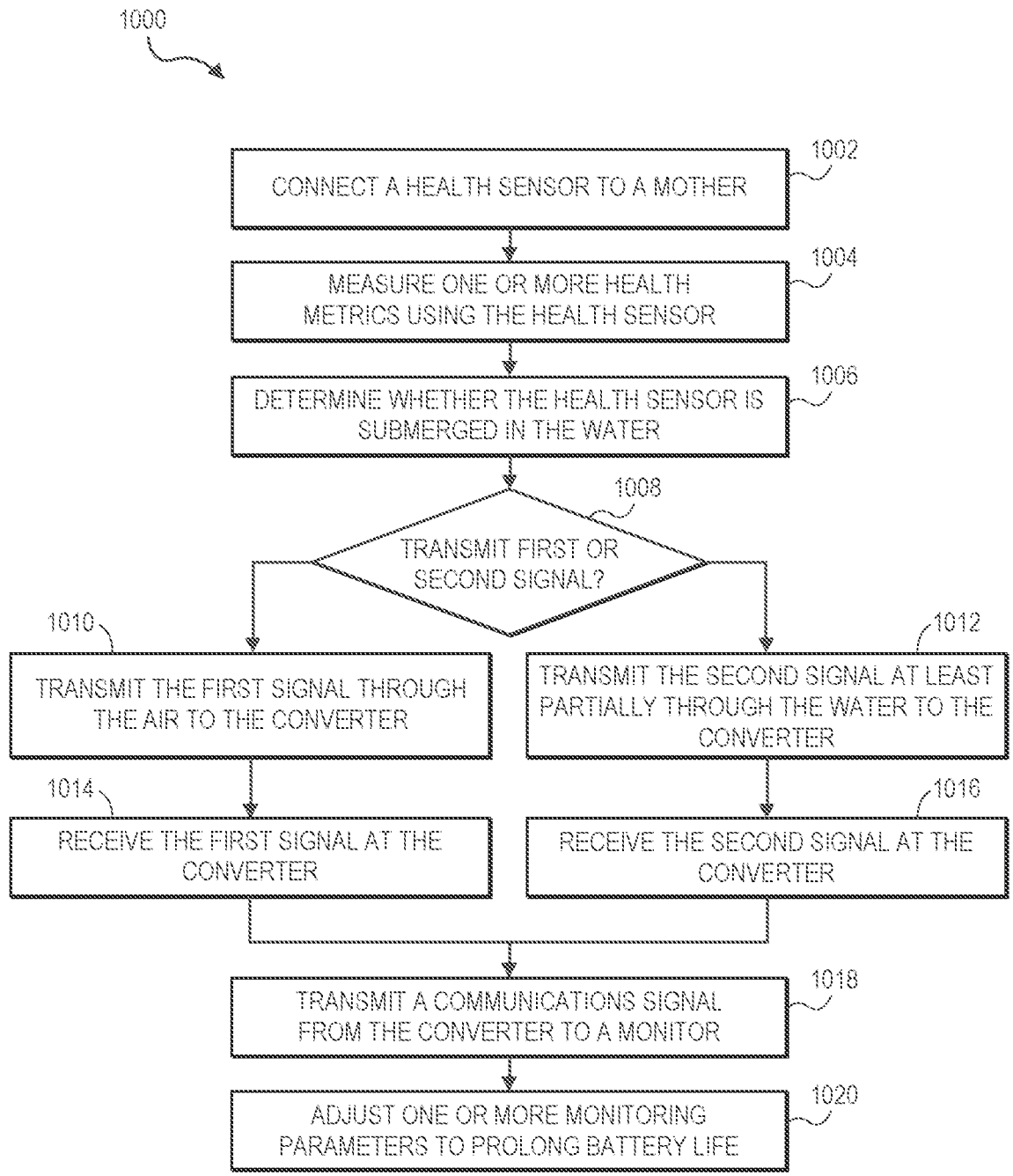
FIG. 10 illustrates a schematic view of another health monitoring system, according to an example.

FIG. 10 illustrates a flowchart of a method 1000 for monitoring a health of a mother, a fetus, or both during a water birth, according to an example. The method 1000 may be executed using one or more of the health monitoring systems discussed herein, or others. Accordingly, the method 1000 should not be considered limited to any particular structure, unless otherwise indicated herein. Moreover, it will be appreciated that the steps of the method 1000 may be combined, separated, performed in parallel or in any sequence, without departing from the scope of the present disclosure.

In an example, the method 1000 includes connecting a health sensor 502 to a mother, as at 1002. The mother is at least partially submerged in a tank 506 of water 508 while the health sensor 502 is connected to her, e.g., after connecting the sensor 502 to the mother, the mother may enter and at least partially submerge in the water 508. The sensor 502 may be secured in any suitable manner, e.g., using straps, bands, etc.

The method 1000 may also include measuring one or more health metrics of the mother, a fetus within the mother, or both while the mother is at least partially submerged, using the health sensor 502, as at 1004. Such monitoring may be accomplished using any type of monitoring device, e.g., ultrasonic transducers such as piezoelectric arrays, as discussed above.

The method 1000 may further include determining whether the sensor 502 connected to the mother is at least partially submerged, as at 1006. Based on this determination, the method 1000 may select whether to transmit a first signal or a second signal, as at 1008.

When the sensor 502 is not submerged, and in response to such determination at 1006, the method 1000 may proceed to transmitting a first signal from health sensor 502 to a converter (e.g., a standalone converter 504 or an integrated hub 600), as at 1010. For example, the sensor 502 may activate (power, switch to) circuitry configured to transmit the first signal. This first signal may not travel through water without significant attenuation, but may be configured to travel through air. As such, the first signal may have a relatively high signal frequency (e.g., 2.5 GHZ or 5 GHZ). It will be appreciated that the first and second signals may be emitted from the same transmitter, but with one or more parameters altered, e.g., frequency, power, etc.

When the sensor 502 is at least partially submerged, and in response to such determination at 1006, the method 1000 may proceed to transmitting a second signal from the health sensor 502 to the converter 504, as at 1012. For example, the sensor 502 may activate circuitry configured to transmit the second signal and de-activate (or otherwise not activate)

circuitry configured to transmit the first signal. The second signal thus travels at least partially through the water to the monitor. In some examples, the second signal may be configured to travel through only water, and thus may be configured to have a relatively low frequency, e.g., 600 MHZ, but may employ a relatively low power, as the signal transmission distance may be constrained by the size of the tank 506. In other examples, the second signal may be configured to travel through both water and air, as discussed above, using a specific MBAN signal. In examples in which the signal travels through both air and water, the device (e.g., the device 906) may be configured to adapt the signal to maintain an EIRP link budget.

The method 1000 may also include receiving the first signals using a first antenna 510 of the monitor 504, as at 1014 and receiving second signals using a second antenna 512 of the monitor 504, as at 1016. Two antennae may be used so as to receive the two signals having the two frequencies, although examples are envisioned using a signal antenna. Moreover, in at least some examples, the first antenna 510 extends above a surface of the water 508 and a second antenna 512 extends below the surface of the water 508.

In some examples, the system 500 includes both a converter 504 and an external health monitoring device 507, which may communicate with one another via a wireless or wired connection. In such examples, the method 1000 may include transmitting one or more communication signals from the converter 504 to the health monitoring device 507, as at 1014. The health monitoring device 507 may be configured to provide a user interface, signal processor, etc. so as to facilitate monitoring the health of the mother, fetus, or both. In other examples, the health monitoring device 507 and the converter 504 may be integrated into a hub 700, as discussed above, and thus transmitting to a converter may refer to transmitting to a hub, and vice versa.

Further, in at least some examples, the method 1000 may also include adjusting one or more monitoring parameters implemented by the health sensor 502 (e.g., via an ultrasonic transducer thereof) as it measures data from the mother, fetus, or both, as at 1016. For example, as noted above, the consistency or distance/depth of the fetal heartrate may be used as a factor to control pulse duration for the ultrasonic signals. A variety of other measures may be used, additionally or instead of the foregoing, in order to preserve battery life of the health sensor 502.

In one or more examples, the functions described can be implemented in hardware, software, firmware, or any combination thereof. For a software implementation, the techniques described herein can be implemented with modules (e.g., procedures, functions, subprograms, programs, routines, subroutines, modules, software packages, classes, and so on) that perform the functions described herein. A module can be coupled to another module or a hardware circuit by passing and/or receiving information, data, arguments, parameters, or memory contents. Information, arguments, parameters, data, or the like can be passed, forwarded, or transmitted using any suitable means including memory sharing, message passing, token passing, network transmission, and the like. The software codes can be stored in memory units and executed by processors. The memory unit can be implemented within the processor or external to the processor, in which case it can be communicatively coupled to the processor via various means as is known in the art.

Figure 11:
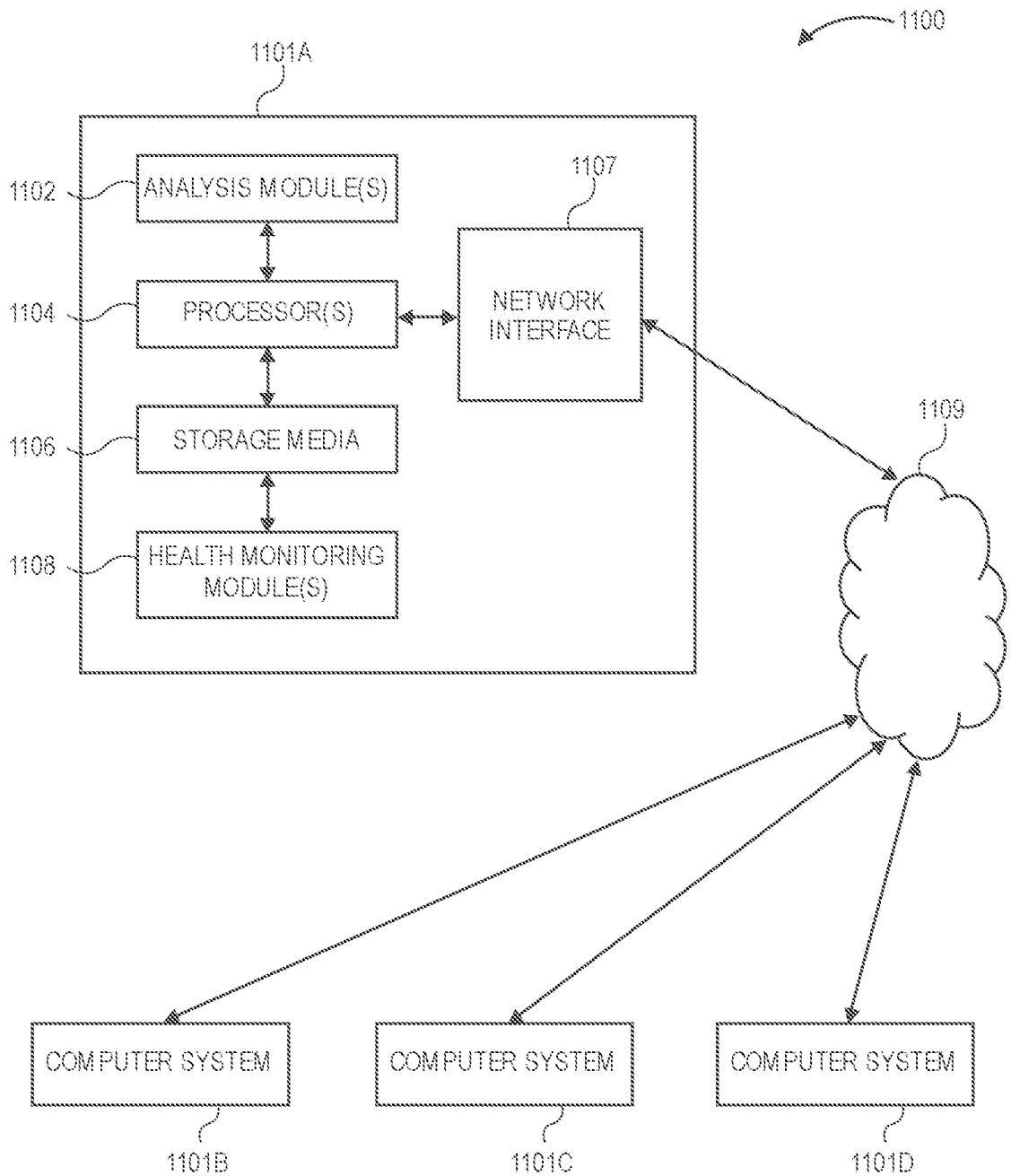
FIG. 11 illustrates an example of such a computing system, in accordance with some examples.

In some examples, any of the methods of the present disclosure may be executed by a computing system. FIG. 11 illustrates an example of such a computing system 1100, in accordance with some examples. The computing system 1100 may include a computer or computer system 1101A, which may be an individual computer system 1101A or an arrangement of distributed computer systems. The computer system 1101A includes one or more analysis module(s) 1102 configured to perform various tasks according to some examples, such as one or more methods disclosed herein. To perform these various tasks, the analysis module 1102 executes independently, or in coordination with, one or more processors 1104, which is (or are) connected to one or more storage media 1106. The processor(s) 1104 is (or are) also connected to a network interface 1107 to allow the computer system 1101A to communicate over a data network 1109 with one or more additional computer systems and/or computing systems, such as 1101B, 1101C, and/or 1101D (note that computer systems 1101B, 1101C and/or 1101D may or may not share the same architecture as computer system 1101A, and may be located in different physical locations, e.g., computer systems 1101A and 1101B may be located in a processing facility, while in communication with one or more computer systems such as 1101C and/or 1101D that are located in one or more data centers, and/or located in varying countries on different continents).

A processor can include a microprocessor, microcontroller, processor module or subsystem, programmable integrated circuit, programmable gate array, or another control or computing device.

The storage media 1106 can be implemented as one or more computer-readable or machine-readable storage media. Note that while in the example of FIG. 11 storage media 1106 is depicted as within computer system 1101A, in some examples, storage media 1106 may be distributed within and/or across multiple internal and/or external enclosures of computing system 1101A and/or additional computing systems. Storage media 1106 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories, magnetic disks such as fixed, floppy and removable disks, other magnetic media including tape, optical media such as compact disks (CDs) or digital video disks (DVDs), BLURAY® disks, or other types of optical storage, or other types of storage devices. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

In some examples, computing system 1100 contains one or more health monitoring signal module(s) 1108. In the example of computing system 1100, computer system 1101A includes the health monitoring signal module 1108. In some examples, a single health monitoring signal module may be used to perform some or all aspects of one or more examples of the methods. In alternate examples, a plurality of health monitoring signal modules may be used to perform some or all aspects of methods.

It should be appreciated that computing system 1100 is only one example of a computing system, and that computing system 1100 may have more or fewer components than shown, may combine additional components not depicted in the example of FIG. 11, and/or computing system 1100 may have a different configuration or arrangement of the components depicted in FIG. 11. The various components shown in FIG. 11 may be implemented in hardware, software, or a combination of both hardware and software, including one or more signal processing and/or application specific integrated circuits.

Further, the steps in the processing methods described herein may be implemented by running one or more functional modules in information processing apparatus such as general purpose processors or application specific chips, such as ASICs, FPGAs, PLDs, or other appropriate devices. These modules, combinations of these modules, and/or their combination with general hardware are all included within the scope of protection of the invention.

As used herein, the terms "inner" and "outer"; "up" and "down"; "upper" and "lower"; "upward" and "downward"; "above" and "below"; "inward" and "outward"; and other like terms as used herein refer to relative positions to one another and are not intended to denote a particular direction or spatial orientation. The terms "couple," "coupled," "connect," "connection," "connected," "in connection with," and "connecting" refer to "in direct connection with" or "in connection with via one or more intermediate elements or members."

The foregoing has outlined features of several examples so that those skilled in the art may better understand the present disclosure. Those skilled in the art should appreciate that they may readily use the present disclosure as a basis for designing or modifying other processes and structures for carrying out the same purposes and/or achieving the same advantages of the examples introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A system for monitoring health during a water birth, the system comprising:
    a health sensor configured to be coupled to a mother, wherein the health sensor comprises:
        a first sensor configured to measure one or more health parameters of a mother, a fetus within the mother or both;
        a second sensor configured to generate a submerged signal representing whether the health sensor is at least partially submerged in water; and
        a transmitter configured to transmit communication signals representing data collected by the first sensor, wherein one or more parameters of the communication signals change depending on whether the submerged signal represents that the health sensor is at least partially submerged.

2. The system of claim 1, wherein the communication signals comprise a first signal having a first frequency and a second signal having a second frequency, the first frequency being higher than the second frequency, wherein the transmitter transmits the first signal when the submerged signal represents that the health sensor is not submerged, and wherein the transmitter transmits the second signal when the submerged signal represents that the health sensor is at least partially submerged.

3. The system of claim 2, wherein the first signal has a higher power than the second signal.

4. The system of claim 2, wherein the health sensor comprises a first antenna configured to emit the first signal and a second antenna configured to emit the second signal.

5. The system of claim 1, wherein the health sensor is configured to adapt the one or more parameters of the communication signals based on Effective Isotropic Radiated Power.

6. The system of claim 1, further comprising a converter having a first receiver configured to receive signals from the health sensor that do not travel through water, and a second receiver configured to receive signals from the health sensor that travel through the water.

7. The system of claim 6, further comprising a monitor in communication with the converter via a wireless or wired connection.

8. The system of claim 6, wherein the first receiver of the converter comprises an antenna that extends above a surface of the water, and wherein the second receiver of the converter comprises an antenna that extends below the surface of the water.

9. The system of claim 1, wherein the first sensor comprises an ultrasonic transducer configured to measure maternal heartrate, fetal heartrate, uterine activity, fetal movement, or a combination thereof.

10. The system of claim 9, wherein the health sensor comprises a power management module configured to adjust one or more parameters of the ultrasonic transducer based at least in part on a location of a detected fetal heartrate, so as to preserve battery life of the health sensor.

11. The system of claim 1, wherein the second sensor is configured to measure an impedance of an antenna of the transmitter, or wherein the second sensor is configured to measure a resistivity of an environment in which the health sensor is positioned, or both.

12. A method for monitoring health during a water birth, comprising:
    connecting a health sensor to a mother;
    measuring one or more health metrics of the mother, a fetus within the mother, or both while the mother is positioned in a tank having water therein, using the health sensor;
    transmitting a first signal from the health sensor to a health monitoring device when the health sensor is not submerged in the water, wherein the first signal does not travel through the water; and
    transmitting a second signal from the health sensor to the health monitoring device when the health sensor is at least partially submerged in the water, wherein the second signal travels at least partially through the water to the health monitoring device.

13. The method of claim 12, further comprising:
    determining that the health sensor is at least partially submerged in the water using a first sensor of the health sensor; and
    selecting to transmit the second signal and not to transmit the first signal in response to determining that the health sensor is at least partially submerged.

14. The method of claim 12, wherein the second signal travels at least partially through the water and at least partially through air to the health monitoring device.

15. The method of claim 12, wherein the first signal has a higher frequency than the second signal.

16. The method of claim 12, further comprising:
    receiving the first and second signals using a converter connected to the tank; and transmitting a communication signal representing data received in the first signal, the second signal, or both from the converter to the health monitoring device.

17. The method of claim 16, wherein receiving the first and second signals using the converter comprises:
   receiving the first signal using a first antenna that extends above a surface of the water; and
   receiving the second signal using a second antenna that extends below the surface of the water.

18. The method of claim 12, further comprising adjusting a monitoring signal transmission parameter of the health sensor based on one or more measurements related to fetal heartrate taken by the health sensor.

19. A system for monitoring health during a water birth, the system comprising:
   a health sensor configured to be coupled to a mother, wherein the health sensor comprises:
      a first antenna for transmitting first signals through air and not through water;
      a second antenna for transmitting second signals at least partially through water, wherein the first signals have a higher frequency than the second signals;
      an ultrasonic transducer configured to measure one or more health parameters of the mother, a fetus within the mother, or both;
      a water sensor configured to detect when the health sensor is at least partially submerged in the water; and
      a switch module connected to the first and second antenna, wherein the switch module is configured to active the first antenna in response to the sensor detecting that the health sensor is not submerged, and wherein the switch module is configured to activate the second antenna in response to the sensor detecting that the health sensor is submerged in the water; and
   a converter, hub, or both configured to receive the first and second signals, wherein the first signals travel through the air to the converter, hub, or both, and wherein the second signals travel at least partially through the water to the converter, hub, or both.

20. The system of claim 19, wherein the converter, hub, or both comprise a first antenna that extends out of the water and a second antenna that extends in the water.

* * * * *